(12) United States Patent
Birnkrant et al.

(10) Patent No.: US 12,414,683 B2
(45) Date of Patent: Sep. 16, 2025

(54) ENDOSCOPE AND ENDOSCOPIC SYSTEM

(71) Applicant: KARL STORZ Endovision, Inc., Charlton, MA (US)

(72) Inventors: Dashiell Birnkrant, Sutton, MA (US); Michael Kloter, Sturbrigdge, MA (US); Marko Radosevic, Goleta, CA (US); Indrek-Toomas Polluks, Rakvere (EE); Pirasanth Sivathasan, Kreuzlingen (CH); Tyrel Waagen, Douglas, MA (US)

(73) Assignee: KARL STORZ Endovision, Inc., Charlton, MA (US)

( * ) Notice: Subject to any disclaimer, the term of this patent is extended or adjusted under 35 U.S.C. 154(b) by 0 days.

(21) Appl. No.: 18/641,080

(22) Filed: Apr. 19, 2024

(65) Prior Publication Data

US 2024/0260825 A1    Aug. 8, 2024

Related U.S. Application Data

(62) Division of application No. 17/552,117, filed on Dec. 15, 2021, now Pat. No. 11,986,164.

(51) Int. Cl.
| | |
|---|---|
| *A61B 1/00* | (2006.01) |
| *A61B 1/045* | (2006.01) |
| *A61B 1/05* | (2006.01) |
| *A61B 1/06* | (2006.01) |
| *A61B 1/12* | (2006.01) |
| *H04N 23/667* | (2023.01) |
| *H04N 23/50* | (2023.01) |

(52) U.S. Cl.
CPC .............. *A61B 1/126* (2013.01); *A61B 1/045* (2013.01); *A61B 1/05* (2013.01); *A61B 1/0655* (2022.02); *H04N 23/667* (2023.01); *H04N 23/555* (2023.01)

(58) Field of Classification Search
CPC ....... A61B 1/126; A61B 1/0655; A61B 1/045; A61B 1/05; H04N 23/555
See application file for complete search history.

(56) References Cited

U.S. PATENT DOCUMENTS

| | | | | |
|---|---|---|---|---|
| 5,191,878 A | * | 3/1993 | Iida | A61B 1/126 |
| | | | | 600/157 |
| 2007/0027359 A1 | * | 2/2007 | Salman | A61B 1/015 |
| | | | | 600/158 |
| 2008/0294008 A1 | * | 11/2008 | Toyama | A61B 1/015 |
| | | | | 600/156 |

* cited by examiner

*Primary Examiner* — Timothy J Neal
(74) *Attorney, Agent, or Firm* — David N. Villalpando; Jacqueline Cohen

(57) ABSTRACT

An endoscopic system and method for its operation are disclosed. The system comprises a light source, an endoscope with a distal light entrance surface, an image sensor capturing images through the light entrance surface and a rinsing device for providing a rinsing fluid flow for rinsing the light entrance surface, the method including the steps of receiving a sensor signal from a sensor detecting a user input starting a rinsing operation of the rinsing device, and, upon receipt of the sensor signal, changing an illumination mode of the light source from a first illumination mode to a second illumination mode and/or changing the video capture from a first video capture mode to a second video capture mode. The second illumination and/or video capture mask undesirable visual artifacts which can occur when collecting images with a rolling shutter sensors while performing a liquid flush of the light entrance surface.

8 Claims, 9 Drawing Sheets

ENDOSCOPE AND ENDOSCOPIC SYSTEM

CROSS REFERENCE TO RELATED APPLICATIONS

This application is a division of U.S. patent application Ser. No. 17/552,117, filed Dec. 15, 2021, entitled "Endoscope, Endoscopic System and Method of Operating the Endoscopic System," that issued as U.S. Pat. No. 11,986,164 on May 21, 2024, and which is incorporated herein by reference.

FIELD

The present invention refers to a method of operating an endoscopic system, an endoscopic system, and in particular methods and systems wherein an objective window may be cleaned in situ by a fluid spray.

BACKGROUND

An image sensor usually comprises a large number of pixels arranged in a matrix. In each pixel, light incident on the pixel produces an electric charge or another electrical signal. In a CCD sensor, all of the sensor pixels are simultaneously sensitive to incident light, therefore, the entire image may be "read" between global resets, mimicking, thereby, conventional moving picture film cameras. This is generally known as a global shutter or global shutter mode. By contrast, CMOS sensors usually operate in a "rolling shutter mode" wherein pixels in different rows are light sensitive in different time intervals, where the light sensitive time interval of each subsequent row is slightly later than that of the previous row. One of the results of a rolling shutter is that when a fast-moving object is captured, a heavily distorted image may be captured as, by the time a subsequent row of pixels is captured, the object will have moved. This is generally known as the rolling shutter effect.

In medical applications such as surgeries, objects of interest to the user rarely move quickly, and thus the rolling shutter effect is not usually a problem during normal operation. However, it is frequently the case that the light entrance interface at the distal end of an endoscope can become contaminated by solid and/or liquid debris that can severely reduce the image quality. In order to address the soiling of the light entrance interface of the endoscope, some endoscopes provide the ability to rinse (or "flush", the terms being used interchangeably in this disclosure) the light entrance surface with a fluid in situ, permitting thereby the cleaning of the distal end without the need to remove the endoscope from the operating theater. This operation is sometimes referred to in this disclosure as a "lens flush" or a "lens rinse," although it should be noted that the surface that is rinsed is not necessarily a lens element, but could be, rather, a cover glass or other optically transparent member, distally placed between the surgical theater and the objective lens system of the endoscope. However, both a rinsing liquid flowing across the light entrance surface and rinsing liquid droplets or debris blown away by a rinsing gas, may result in a distracting/disturbing rolling shutter effect for endoscopes using CMOS sensors, as these fast moving objects move through the field of view. Additionally, bright illumination light can cause bright reflections from liquid droplets present on the distal light entrance surface or rinsing liquids being sprayed in the field of view, and these bright reflections are also distorted by the rolling shutter effect. The resulting optical experience can be perceived by medical personnel as a disturbing or an incorrect indication that the optical or electronic apparatus is broken or not working properly.

In U.S. Pat. No. 9,801,530 B2, an endoscope apparatus having a CMOS type solid-state image pickup element and an image pickup control method are described. A fluid detection device detects a fluid operation based on an object region edged along a direction parallel to scan lines of the image pickup element. An exposure control device lengthens an exposure time if the fluid operation detection device detects the fluid operation. If an edging phenomenon is detected the driving method of an image pickup element 58 is switched to a pseudo-global shutter method. The method of operating a CMOS sensor in a pseudo-global shutter mode is known in the art, accordingly U.S. Pat. No. 9,801,530 B2 by Kagaya, et al, entitled, "Endoscope Apparatus and Image Pickup Control Method Thereof," issued Oct. 31, 2017, is incorporated by reference.

SUMMARY

An object of the present invention is to provide an improved method of operating an endoscopic system, an improved endoscope, an improved rinsing device, an improved camera control unit and an improved endoscopic system.

Some embodiments of the present invention address the problems associated with image collection by sensors with a rolling shutter by changing an illumination mode and optionally also a capturing mode when a sensor signal is received from a sensor detecting a user input starting a rinsing operation. For this purpose, some of the embodiments detect a manual operation of a valve controlling a flow of the rinsing fluid and/or gas by detecting a pressure or a change of pressure or a flow or a change of flow of rinsing fluid.

A method of operating an endoscopic system is presented. The endoscopic system includes a light source, an endoscope with a distal light entrance surface, an image sensor for capturing images through the light entrance surface, a rinsing device providing a rinsing fluid flow for rinsing the light entrance surface, a pressure sensor, and a flush detection module. The pressure within the rinsing device is monitored for deviations from an expected pressure, indicating an impulse event. The impulse event is analyzed to determine if it is indicative of a flush impulse even, that is, matches a pressure signature corresponding to the closing of a valve resulting in a liquid flush/rinse of the light entrance surface of the endoscope. The monitoring of the pressure within the rinsing device is also monitored in order to determine the slope of the pressure change in the system. Analysis of the slope and the impulse event allow the determination of the flush mode, and when a flush of the distal light entrance surface is determined to be active, the video settings of the system are changed from a first to a second video mode.

Another aspect of the invention is to further analyze the pressure signal to determine when the flush has ended and switching back from the second to the first video mode.

In some aspects of the invention, the first video mode may include operating the intensity of the light source at a first illumination level, and then decreasing the intensity in the second illumination mode. Another possible implementation of the invention is one where the first video mode is one wherein the image sensor operates in a rolling shutter mode and operates in a pseudo-global shutter mode for the second video mode. In some implementations it is advantageous to gradually increase the illumination intensity when transitioning from the second video mode back to the first video mode, particularly when operating in a rolling shutter mode.

In some implementations of the inventive method, the detection of the impulse event is performed by an impulse determination module, the determination of the slope is performed by a slope determination module, and the determination of the flush impulse event is performed by a state determination module. These modules may all be elements of flush determination module and may be elements of a processor present in a camera control unit or another processor present in the system, such as within the endoscope itself of as an element of the rinsing device.

In some implementations of the invention the transition from the second video mode back to the first may happen at a predetermined period of time after the detection of the end of the flushing mode, such as several seconds after the detection of the end of the flush. In some implementations of the method, before switching back to the first video mode, the slope determination module may be monitored until a zero slope is maintained for a predetermined amount of time.

An endoscopic system for minimizing display anomalies occurring during a flush of the distal light entrance surface is also presented. The system includes an endoscope with a shaft, a light entrance surface at the distal end of the shaft, through which light from an image scene pass and are captured by an electronic image sensor. Within the shaft are a liquid rinsing duct and a gas rinsing duct, the ducts conducting fluids from the proximal end of the endoscope to the light entrance surface. A valve is present for opening and closing the gas rinsing duct, which is controlled by a user interface, such as a button on the endoscope. The system also includes a rinsing device with a pump that has fluid connections to a rinsing liquid reservoir and to the endoscope. A pressure sensor detects the pressure within a fluid connection of the rinsing device and sends pressure data to flush detection module.

In another implementation of the system, the user interface includes a passageway whereby gas may pass from the pump to the environment. When this passageway is obstructed, the gas is directed to the distal tip of the endoscope. In some implementations, the user interface may also be operated to completely block the flow of gas from the pump through the endoscopic shaft, thereby increasing the pressure to the liquid reservoir, and causing rinsing liquid to flow therefrom to the distal end of the endoscope, where it can be used to rinse the distal light entrance surface.

In various implementations, the flush detection module includes an impulse detection module, a slope determination module, and a state determination module. These modules may be elements of a camera control unit in communication therewith. The camera control module can then change from a first video capture mode to a second video capture mode when a flush event is occurring.

In some implementations, the endoscopic system includes a light source in communication with the camera control unit, and the camera control unit can issue commands to the light source in order to decrease the illumination intensity when changing from a first illumination mode to a second illumination mode.

In some implementations the endoscopic system includes a plug element that is detachably connectable to the endoscope and may have the flush detection module as an element thereof, which may or may not include the pressure sensor.

BRIEF DESCRIPTION OF THE DRAWINGS

Embodiments will be described below with reference to the enclosed figures.

FIG. 11 shows representative data received by a pressure sensor and used to determine the flush state.

DETAILED DESCRIPTION

Figure 1:
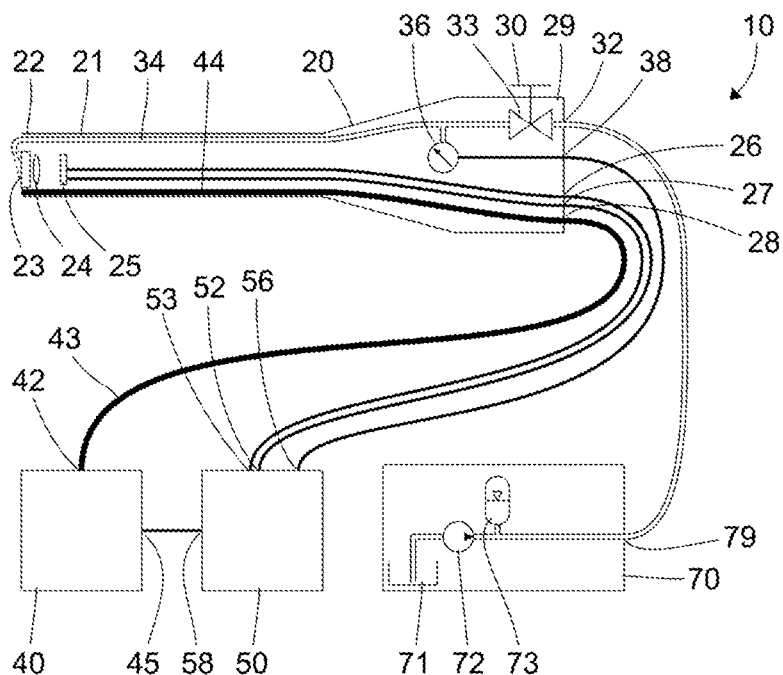
FIG. 1 shows a schematic representation of an endoscopic system.

FIG. 1 shows a schematic representation of and endoscopic system 10 comprising an endoscope 20, a light source 40, a camera control unit 50 and a rinsing device 70. The endoscopic system 10 can be provided and configured for medical purposes, in which case the endoscope 20 may be hermetically sealed to tolerate the temperature, pressure, and atmosphere during steam sterilization in an autoclave. As an alternative, the endoscopic system 10 can be configured for non-medical, industrial applications. Industrial endoscopes are often referred to as "borescopes." Throughout this disclosure the term "endoscope" shall be understood to mean both medical endoscopes and borescopes.

The endoscope 20 comprises a long and thin shaft 21. The shaft 21 can be entirely rigid or partially rigid and partially flexible or entirely flexible. The shaft 21 is usually configured to be inserted into a body cavity of a human or animal patient.

At a distal end 22 of the shaft 21, light emanating from an object within an object scene can enter the endoscope 20 through a distal light entrance surface 23, often a cover glass or a flat element of an objective lens system. A lens 24 downstream from the distal light entrance surface 23 forms a real image onto an image sensor 25. In the example shown in FIG. 1, the image sensor 25 is located at the distal end 22 of the endoscope. Alternatively, the real image produced by the lens 24 can be transferred to the proximal end 29 of the endoscope 20 by a relay lens system or by a bundle of optical fibers. In this case, the image sensor 25 can be located at the proximal end 29 of the endoscope 20 or in a camera or another device optically coupled to the proximal end 29 of the endoscope. The camera (or "camera head") may be permanently or detachably coupled to the shaft.

The endoscope 20 comprises an image sensor control input 26, receiving an image sensor control signal from the camera control unit 50. The image sensor control input 26 is coupled to the image sensor 25. Parameters such as the frame rate, the size of the image, the exposure time, the sensitivity or electronic gain to be applied by the image sensor 25 itself, and timing information can be part of the image sensor control signal.

Additionally, the endoscope 20 has an image signal output 27 that provides an analog or digital image signal generated by the image sensor 25 and represents a real image produced by the lens 24 and captured by the image sensor 25. In the present example, the image signal provided at the image signal output 27 may be transferred to the camera control unit 50. Both the image sensor control input 26 and the image signal output 27 may be situated at the proximal end 29 of the endoscope 20. The image sensor control input 26 and the image signal output 27 can be integrated in one connector transferring both the image sensor control signal and the image signal in opposite directions.

The endoscope 20 additionally comprises an illumination light input 28, that receives illumination light from the light source 40. Illumination light received at the illumination light input 28 is guided by one or more optical fibers 44, or other illumination transfer means, to the distal end 22 of the endoscope and radiated on an object within an object scene to be viewed. In the example shown in FIG. 1, the illumination light input 28 is situated at the proximal end 29 of the endoscope 20.

The endoscope 20 also comprises a user interface 30 at the proximal end 29. In the example shown in FIG. 1, the user interface 30 comprises a button which can be manually pressed. A rinsing fluid input 32 is provided at the proximal end 29 of the endoscope 20. A valve 33 connects the rinsing fluid input 32 to a rinsing fluid duct 34. The rinsing fluid duct 34 connects the valve 33 with a rinsing fluid outlet at the distal end 22 of the endoscope 20. The user interface 30 is coupled to a valve member of the valve 33. Rinsing fluid flow to the distal end 22 of the endoscope can be controlled by manual operation of the user interface 30.

A pressure sensor 36 is coupled to the rinsing fluid duct 34 downstream from the valve 33 and detects the pressure in the rinsing fluid duct 34. The pressure sensor 36 is coupled to a sensor signal output 38 at the proximal end 29 of the endoscope 20. A sensor signal produced by the pressure sensor 36 and representing the pressure in the rinsing fluid duct 34 detected by the pressure sensor 36, or a change of the pressure, is provided at the sensor signal output 38. The senor signal output 38 is coupled to the camera control unit 50.

In the example shown in FIG. 1, the sensor signal output 38 is shown as a separate connector. Alternatively, the sensor signal output 38 can be integrated with the image sensor control input 26 and/or with the image signal output 27.

The light source 40 includes an illumination light output 42 coupled to the illumination light input 28 by a light guiding cable 43. Illumination light produced by the light source 40 is transferred to the illumination light input 28 of the endoscope through the light guiding cable 43. In the endoscope 20, optical fibers 44 guide the illumination light to the distal end 22 of the endoscope 20 where it exits the endoscope 20 and illuminates an object to be viewed. The light source 40 comprises a control input 45 receiving a control signal from the camera control unit 50.

The camera control unit 50 provides an image sensor control output 52 coupled to the image sensor control input 26 of the endoscope 20, an image signal input 53 coupled to the image signal output 27 of the endoscope 20, and a sensor signal input 56 coupled to the sensor signal output 38 of the endoscope 20. The sensor signal input 56 can be integrated in one connector together with the image sensor control output 52 and/or with the image signal input 53. In this case, the sensor signals produced by the pressure sensor 36 and/or image sensor control signals and/or image signals can be transferred via the same wires or fibers. The camera control unit 50 also includes a control output 58 coupled to the control input 45 of the light source.

The rinsing device 70 comprises a rinsing fluid reservoir 71 supplying rinsing fluid. In the example shown in FIG. 1, the rinsing fluid reservoir 71 contains a rinsing liquid, and the rinsing device 70 includes a rinsing fluid pump 72 that draws rinsing liquid from the rinsing fluid reservoir 71 and a pressure reservoir 73. The rinsing device 70 can comprise further components not shown in FIG. 1 such as a pressure sensor for detecting the pressure produced by the rinsing fluid pump 72; a controller for controlling the rinsing fluid pump 72 depending on the pressure detected by the pressure sensor; and a user interface.

As an alternative, the rinsing fluid reservoir 71 can be a rinsing gas reservoir, in particular a pressure vessel containing pressurized gas, for example carbon dioxide, nitrogen or air. In this case, the rinsing fluid pump 72 and the pressure reservoir 73 can be replaced by a pressure reducer reducing the pressure of the gas from the gas vessel to a predetermined value.

As a further alternative, the rinsing device 70 can comprise both a rinsing liquid reservoir 71 together with a rinsing fluid pump 72 and a pressure reservoir 73 and a gas vessel providing a rinsing gas together with a pressure reducer. In this case, the rinsing device 70 can comprise a controller controlling a predetermined procedure or sequence. In particular, the procedure comprises providing a rinsing liquid within a first period of time and, thereafter, providing a rinsing gas in a second period of time, the rinsing gas blowing away or drying rinsing liquid droplets or a rinsing liquid film on the distal light entrance surface 23 of the endoscope.

The rinsing device 70 comprises a rinsing fluid output 79 coupled to the rinsing fluid input 32 of the endoscope by a flexible tube or hose. If the rinsing device 70 provides both a rinsing liquid and a rinsing gas, both can be provided at two different rinsing fluid outputs 79 and conducted to the endoscope 20 by two distinct flexible tubes or hoses. As an alternative, both the rinsing liquid and the rinsing gas can be provided at the same rinsing fluid output 79 and conducted to the endoscope 20 by the same flexible tube or hose.

A user can initiate a rinsing operation by opening the valve 33 by a manual operation of the user interface 30, such as by pressing a push button. When the valve 33 is open, rinsing fluid provided by the rinsing device 70 flows through the rinsing fluid duct 34 to the distal end 22 of the endoscope 20 and rinses the distal light entrance surface 23 of the endoscope 20. The user can stop the rinsing fluid flow by another manual operation of the user interface 30, for example releasing the push button, thereby closing the valve 33. As an alternative, the valve 33 may automatically close after a predetermined period of time that is set to a duration usually sufficient to remove debris from the distal light entrance surface 23.

If the rinsing device 70 provides both a rinsing liquid and a rinsing gas, two valves 33 can be provided and can be manually operated separately, one valve controlling the rinsing liquid flow, and the other valve controlling the rinsing gas flow. Alternatively, the valve 33 controlling the rinsing liquid flow may be directly controlled by a manual operation of the user interface 30, and a second valve controlling the rinsing gas flow may automatically open and allow a rinsing gas to flow for a predetermined duration after the end of the rinsing liquid flow. As a further alternative, the user input at the user interface 30 may open the valve 33 controlling the rinsing liquid flow, but a controller closes the valve 33 thereby stopping the rinsing liquid flow after a first predetermined period of time, and thereafter opens a second valve controlling the rinsing gas flow for a second predetermined period of time.

When a rinsing fluid is flowing through the rinsing fluid duct 34, the pressure in the rinsing fluid duct 34 is higher than when there is no rinsing fluid flow. Due to the flow resistance of the rinsing fluid duct 34, the pressure of the rinsing fluid immediately downstream from the valve 33 is higher when the valve 33 is open. Immediately after opening the valve 33, the pressure increases, and immediately after closing the valve 33, the pressure decreases. Therefore, the pressure of the rinsing fluid in the rinsing fluid duct 34 detected by the pressure sensor 36 indicates the beginning and the end of a rinsing operation.

The camera control unit 50 receives, at its sensor signal input 56, the sensor signal from the pressure sensor 36. The camera control unit 50 controls the light source 40 by a control signal provided at the control output 58 of the camera control unit 50 and received by the light source 40 at its control input 45.

During normal use of the endoscopic system 10, i.e., when there is no rinsing operation, the light source 40 is in a first illumination mode. Details of the first illumination mode, such as power or intensity and the spectral characteristics (like color temperature) can be optionally controlled by a user at a user interface.

At the beginning of a rinsing operation, the light source 40 is set to a second illumination mode different from the first illumination mode. As described in more detail below with reference to FIG. 7, the second illumination mode can differ from the first illumination mode in the intensity or power of the illumination light or in the time dependence of the intensity or power, for example. When the end of the rinsing operation is detected, the light source 40 instantaneously or gradually returns to the first illumination mode.

The rinsing device 70 can include a valve at its rinsing fluid output 79 preventing leakage or unintended output of rinsing fluid from the rinsing fluid output 79 when no tube or hose is connected to the rinsing fluid output 79 or when no endoscope 20 is connected to the downstream end of the tube or hose.

During rinsing operation, the camera control unit 50 optionally not only controls a second illumination mode of the light source 40, but simultaneously a second capturing mode of the image sensor 25, different from a first capturing mode controlled when there is no rinsing operation. In the second capturing mode, the exposure time of each single image captured by the image sensor 25 is set to a maximum value. When the exposure time is at a maximum, the reset signal immediately follows on the read signal for each pixel. Therefore, if the image sensor 25 is a CMOS-sensor with a rolling shutter, there is a well-defined period of time called the vertical blanking interval during which all the pixels are able to collect light simultaneously.

Figure 2:
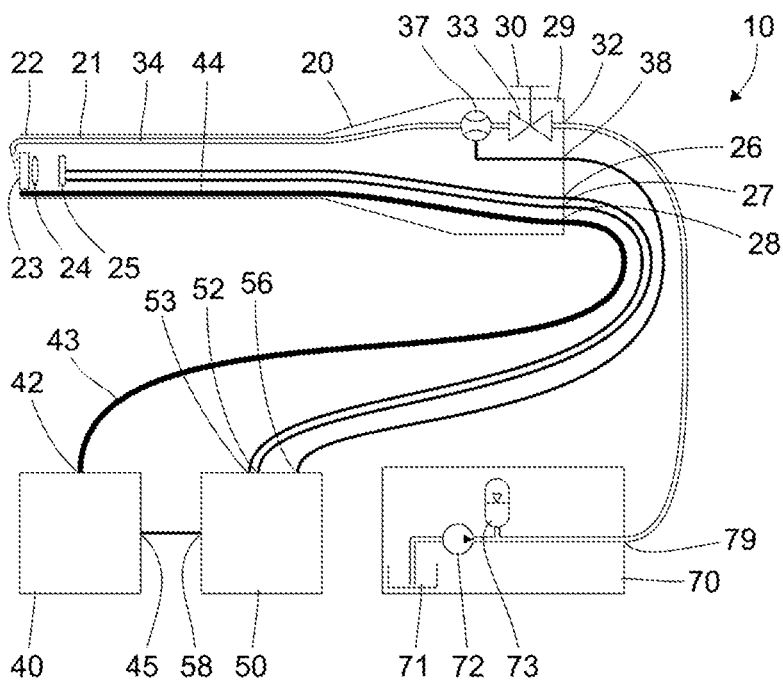
FIG. 2 shows a schematic representation of another endoscopic system.

FIG. 2 shows a schematic representation of another endoscopic system 10 similar to the endoscopic system described with reference to FIG. 1. Only differences of the endoscopic system 10 shown in FIG. 2 from the endoscopic system described above with reference to FIG. 1 are described. In the endoscopic system 10 shown in FIG. 2, the endoscope 20 comprises a flow sensor 37 in the rinsing fluid duct 34. The flow sensor 37 detects the mass flow or the volume flow in the rinsing fluid duct 34 and provides a sensor signal representing the detected mass flow or volume flow of the rinsing fluid in the rinsing fluid duct 34. The camera control unit 50 receives the sensor signal from the flow sensor 37 and controls the light source 40. When the rinsing fluid flow detected by the flow sensor 37, and represented by the sensor signal, increases, indicating the beginning of a rinsing operation, the light source 40 is set to the second illumination mode. When the rinsing fluid flow detected by the flow sensor 37 and represented by the sensor signal decreases, indicating an end of the rinsing operation, the light source 40 is instantaneously or gradually reset to the first illumination mode.

Figure 3:
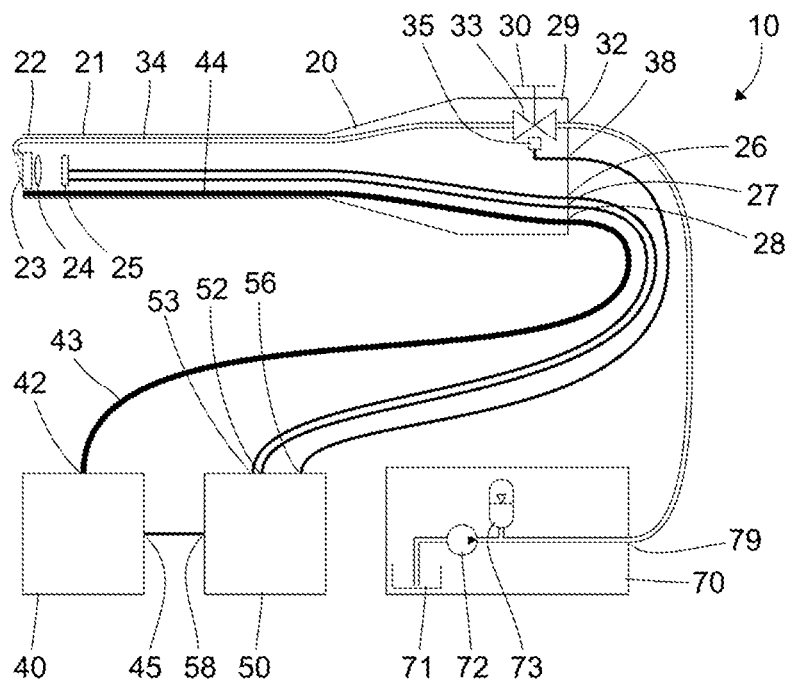
FIG. 3 shows a schematic representation of another endoscopic system.

FIG. 3 shows a schematic representation of another endoscopic system 10 similar to the endoscopic systems described with reference to FIGS. 1 and 2. Only differences of the endoscopic system 10 shown in FIG. 3 from the endoscopic systems described above with reference to FIGS. 1 and 2 are described. In the endoscopic system 10 shown in FIG. 3, the endoscope 20 comprises a Hall sensor 35 located near the valve 33. The Hall sensor 35 detects the magnetic field produced by a permanent magnetic valve member of the valve 33 or the magnetic field of a permanent magnet mechanically coupled to the valve member of the valve 33 or the magnetic field produced by a stationary permanent magnet and altered by the valve member of the valve 33. The magnetic field detected by the Hall sensor 35 depends on the (translational or rotational) position of the valve member of the valve 33 and indicates whether the valve 33 is closed or open. Thus, the sensor signal provided by the Hall sensor 35 and received at the sensor signal input 56 of the camera control unit 50 indicates the closed or open status of the valve 33, and thus the beginning and the end of rinsing operation. Similar to the embodiments described above with reference to FIGS. 1 and 2, the light source 40 is set to the second illumination mode at the beginning of a rinsing operation and instantaneously or gradually reset to the first illumination mode at the end of a rinsing operation.

Figure 4:
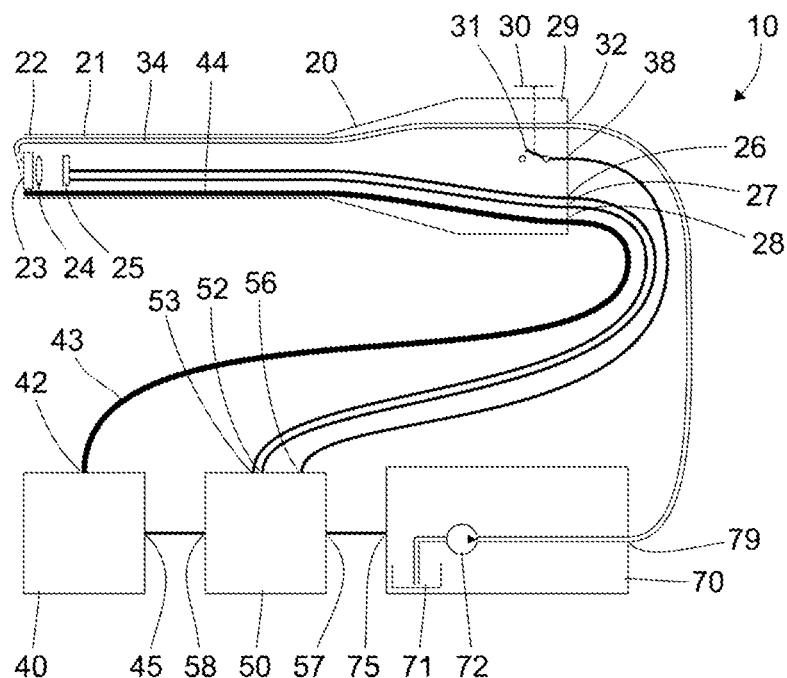
FIG. 4 shows a schematic representation of another endoscopic system.

FIG. 4 shows a schematic representation of another endoscopic system 10 similar to the endoscopic systems described with reference to FIGS. 1 through 3. Only differences of the endoscopic system 10 shown in FIG. 4 from the endoscopic systems described above with reference to FIGS. 1 through 3 are described. In the endoscopic system 10 shown in FIG. 4, the endoscope 20 comprises a user interface sensor 31 detecting a manual input at the user interface 30. In the example shown in FIG. 4, the user interface sensor 31 is an electrical switch and the user interface 30 is a push button. When the push button 30 is manually pressed, the switch 31 closes a circuit, thereby, for example, altering the voltage at a signal line. This sensor signal is received at the sensor signal input 56 of the camera control unit 50. The camera control unit 50 comprises a control output 57 coupled to a control input 75 of the rinsing device 70. When the camera control unit 50 receives a sensor signal indicating a user input at the user interface 30, the camera control unit 50 controls the light source 40 to switch from the first illumination mode to a second illumination mode and controls the rinsing device 70 to perform a rinsing operation, specifically, the conveyance of rinsing fluid by the rinsing fluid pump 72. When the push button 30 is released, or after a predetermined period of time, the camera control unit 50 controls the rinsing device 70 to stop the rinsing operation, by causing the fluid pump to stop conveying rinsing fluid and causing the light source 40 to switch back to the first illumination mode.

Figure 5:
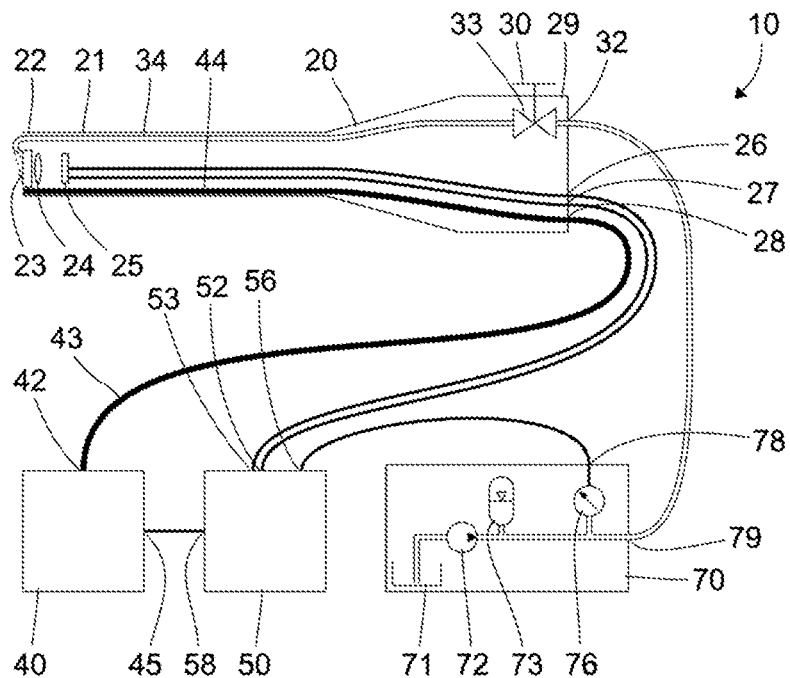
FIG. 5 shows a schematic representation of another endoscopic system.

FIG. 5 shows a schematic representation of another endoscopic system 10 similar to the endoscopic systems described with reference to FIGS. 1 through 4. Only differences of the endoscopic system 10 shown in FIG. 5 from the endoscopic systems described above with reference to FIGS. 1 through 4 are described. The endoscopic system 10 shown in FIG. 5 is similar to the endoscopic system of FIG. 1, but the pressure sensor 36 in the endoscope 20 is replaced by a pressure sensor 76 in the rinsing device 70. The sensor signal input 56 of the camera control unit 50 is connected to a sensor signal output 78 of the rinsing device 70 providing the sensor signal generated by the pressure sensor 76. Due to the flow resistance of the duct between the pressure reservoir 73 and the pressure sensor 76, the pressure sensor 76 detects a decrease of rinsing fluid pressure when the valve 33 in the endoscope 20 is open and rinsing fluid flows from the distal end 22 of the endoscope 20. Therefore, a decrease of pressure represented by the sensor signal received by the camera control unit indicates the beginning of a rinsing operation and an increase of pressure indicates the end of the rinsing operation. The camera control unit can control the illumination mode of the light source 40 and the capturing mode of the image sensor 25 dependent on the sensor signal received from the pressure sensor 76.

Figure 6:
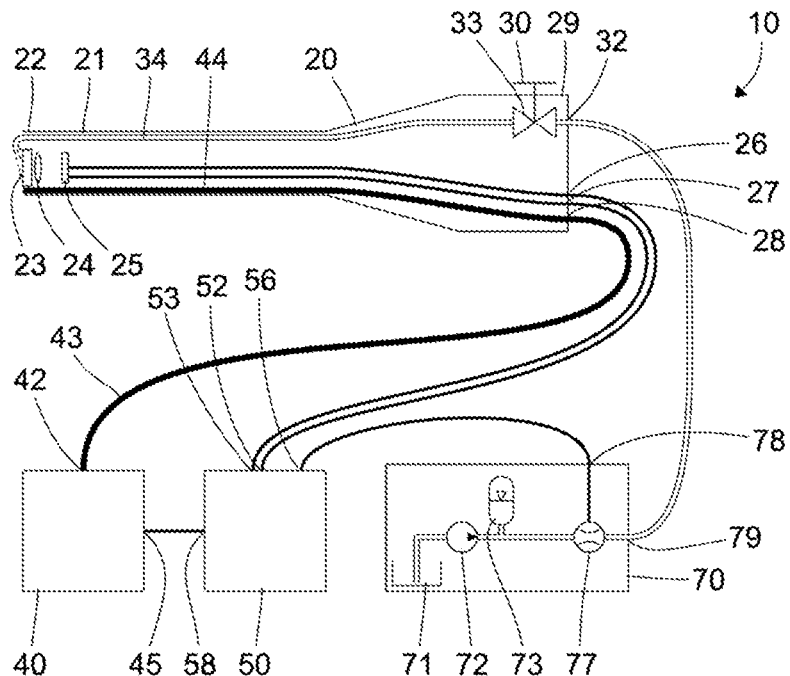
FIG. 6 shows a schematic representation of another endoscopic system.

FIG. 6 shows a schematic representation of another endoscopic system 10 similar to the endoscopic systems described with reference to FIGS. 1 through 5. Only differences of the endoscopic system 10 shown in FIG. 5 from the endoscopic systems described above with reference to FIGS. 1 through 4 are described. The endoscopic system 10 shown in FIG. 6 is similar to the endoscopic system described above with reference to FIG. 2, but the flow sensor 37 in the endoscope 20 is replaced by a flow sensor 77 in the rinsing device 70. Similar to the endoscopic system 10 described above with reference to FIG. 5, the sensor signal input 56 of the camera control unit 50 is coupled to a sensor signal output 78 of the rinsing device 70 providing the sensor signal produced by the flow sensor 77. A rinsing fluid flow detected by the flow sensor 77 indicates an ongoing rinsing operation. Therefore, the camera control unit 50 can control the illumination mode of the light source 40 and the capturing mode of the image sensor 25 dependent on the sensor signal received from the flow sensor 77.

In the modifications of each of the embodiments described above with reference to FIGS. 1 through 6, the light source 40 can be partially or fully integrated in the endoscope 20. In particular, one or more light emitting diodes can be located at the distal end 22 of the endoscope or at the proximal end 29 of the endoscope 20 and coupled to the distal end 22 by one or more optical fibers. Furthermore, one or more semiconductor lasers or other lasers can be located in the endoscope 20 and provide excitation light exciting fluorescence in tissue for diagnostic purposes.

In further modifications of each of the embodiments described above with reference to FIGS. 1 through 6, a part of or the entire camera control unit 50 can be integrated in the endoscope 20. In particular, the above-described control of the illumination mode of the light source 40 and of the capture mode of the image sensor 25 can be provided by a controller located in the endoscope 20.

Figure 7:
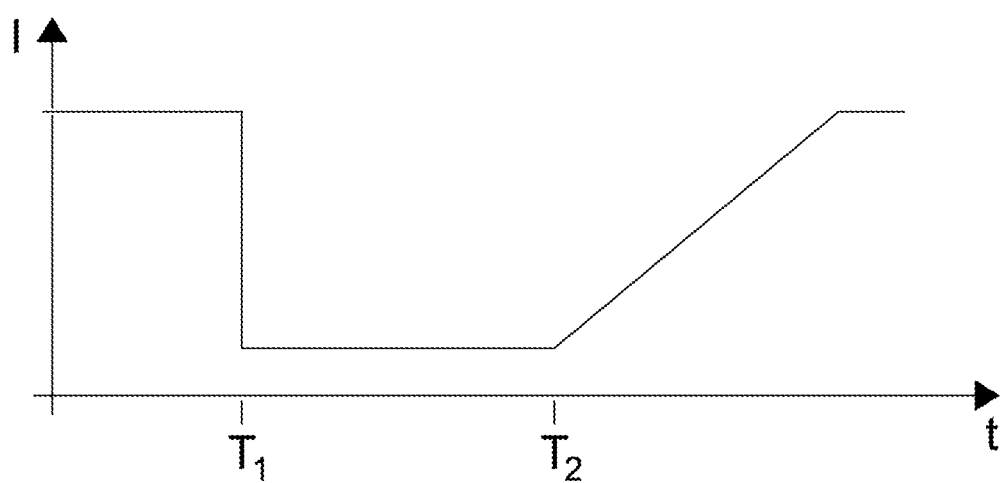
FIG. 7 shows a schematic representation of another time dependence of an intensity of illumination light.

FIG. 7 shows a schematic diagram of time dependence of the intensity I provided by the light source. The intensity I may be set at a maximum desired value in the initial illumination mode. The illumination intensity is reduced to a point that is constant but non-zero in the second illumination mode between times T1 and T2. For example, the intensity may be reduced to about 15% of the intensity in the first illumination mode. In practice, decreasing the illumination value to about 5% of its maximum value has proven to be optimal. Exposure integration time can be controlled by the camera control unit, or automatically by image sensor, as the exposure time is increased in response to the lower illumination of the object scene. In some preferred embodiments, the exposure time, as a result of the lowered illumination intensity, will be at or near the maximum exposure time of a given CMOS image sensor. This increase of exposure time induces or increases motion blur, as is understood in the art, thereby reducing the unwanted rolling shutter effect. The return to the first illumination mode is not necessarily instantaneous in some embodiments. In the example shown in FIG. 7, the light source gradually returns to the first illumination mode starting at time T2, and the intensity is gradually increased until it reaches the original value. This can improve the user experience by producing a smoother transition between the video capture modes without abrupt changes in the image quality.

Figure 8:
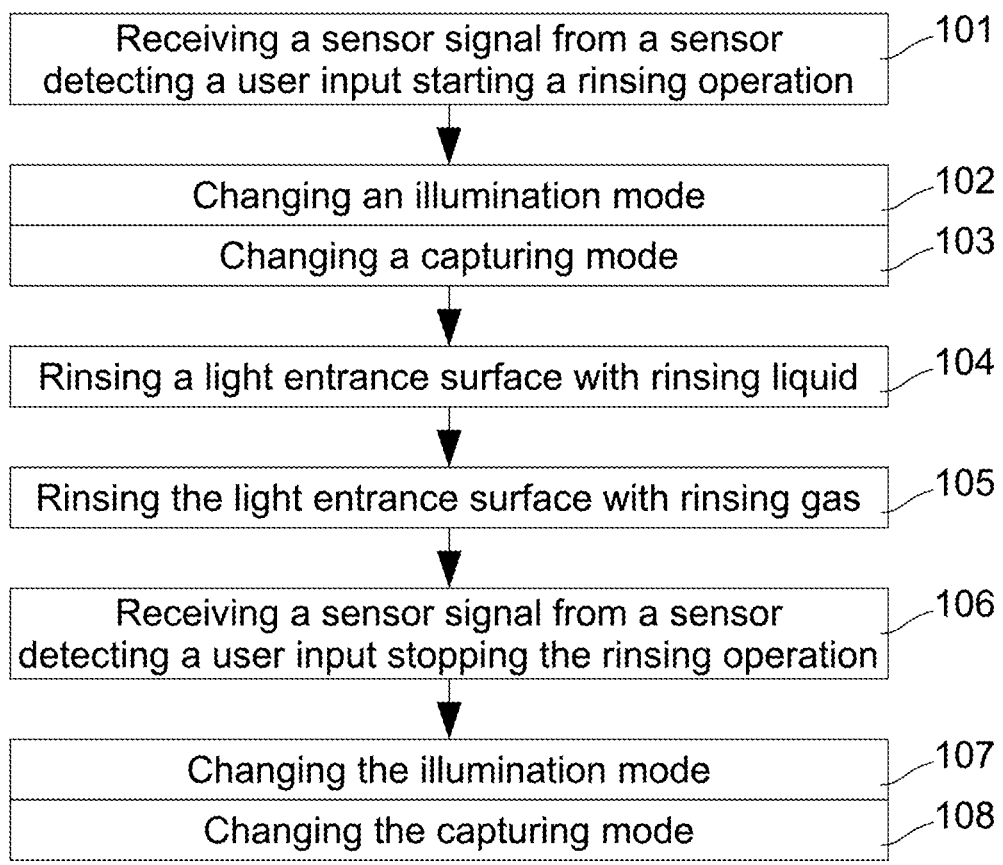
FIG. 8 is a flowchart of a method of operating an endoscopic system.

FIG. 8 is a schematic flowchart of a method of operating an endoscopic system. The method can be applied to one of the endoscopic systems described above with reference to FIG. 1 to 6 or to another different endoscopic. Therefore, hereinafter reference numerals of the embodiments described above with reference to FIGS. 1 through 6 are used as examples only. In a first step 101, the sensor signal, detecting a user input staring a rinsing operation is received from a sensor 31, 35, 36, 37, 76, 77. The sensor can be coupled to a user interface 30, like a switch 31 operated by a push button mechanically, wherein the push button is the user interface 30. Alternatively, the sensor can be coupled to the user interface magnetically, such as by use of a Hall sensor 35 detecting the position or the change of position of a valve member which is directly coupled to the user interface. As a further alternative, the sensor can be coupled to the user interface 30 hydraulically or pneumatically, wherein the user interface 30 directly alters a rinsing fluid flow and the sensor 36, 37, 76, 77 detects the resulting change of rinsing fluid flow or rinsing fluid pressure. When a sensor signal indicating a user input starting a rinsing operation is received, an illumination mode is changed 102 from a first illumination mode to a second illumination mode, and/or a capturing mode is changed 103 from a first capturing mode to a second capturing mode. Examples of first and second illumination modes and first and second capturing modes are described above with reference to FIG. 7. As a result of the user input at the user interface, the light entrance surface 23 is rinsed with rinsing liquid. The light entrance surface 23 can be rinsed with rinsing liquid for a predetermined period of time or as long as the user wishes. After rinsing 104 the light entrance surface with rinsing liquid, the light entrance surface 23 is optionally rinsed 105 with rinsing gas drying a rinsing liquid film on the light entrance surface 23 and/or blowing away any remaining rinsing liquid droplets thereon. The rinsing gas can rinse 105 the light entrance surface 23 within a predetermined period of time or, in some embodiments, as long as a user wishes.

When the rinsing operation comprising rinsing 104 with rinsing liquid and optionally also rinsing 105 with rinsing gas is terminated, a sensor signal is received 106 from a sensor 31, 35, 36, 37, 76, 77 detecting a user input stopping the rinsing operation. The user input stopping the rinsing operation can comprise releasing a button, for example. Alternatively, the signal from a controller controlling the rinsing operation and ending the rinsing operation can be received or a signal from a sensor detecting the end of the rinsing operation (regardless of whether it is caused by a controller or by a user input) can be received. When the sensor signal indicating the user input stopping the rinsing operation or indicating an end of the rinsing operation is received 106, the illumination mode is changed 107 back to the first illumination mode and/or the capturing mode is changed 108 back to the first capturing mode as appropriate. In some embodiments step 102 and 103 may both occur, that is the illumination mode and the capturing mode will both be changed, and then steps 107 and 108 with both occur, that is changing both the illumination mode and the capture mode return to their original states.

The embodiments described above with reference to FIGS. 1 through 7 are provided and configured to perform or conduct the method described above with reference to FIG. 8. As an alternative, each of the embodiments described above with reference to FIGS. 1 through 7 can be provided and configured to conduct or perform a method different from the method described above with reference to FIG. 8.

Particular endoscopic systems, related means of detecting fluid flush modes, and means to compensate for the artifacts induced by the rolling shutter nature of CMOS sensors commonly used in endoscopes have been presented above. However, in some endoscopic systems shown, in particular those of FIGS. 2, 3, 4, and 6, the flush modes are detected by an electronic signal resulting from the user input or a direct detection of liquid flow. However, it is a further objective of this invention to provide positive flush start and stop detection independent of any electrical signal directly generated by the user interface 30 or a liquid flow sensor. This advantage of the present invention is particularly important in enabling a corrective display for endoscopes already in the field, without the need to extensively retrofit the instruments, create new models, or provide extensive hardware improvements, providing thereby "software-only" solutions or software solutions with minimal changes to existing endoscopic systems.

Figure 9A:
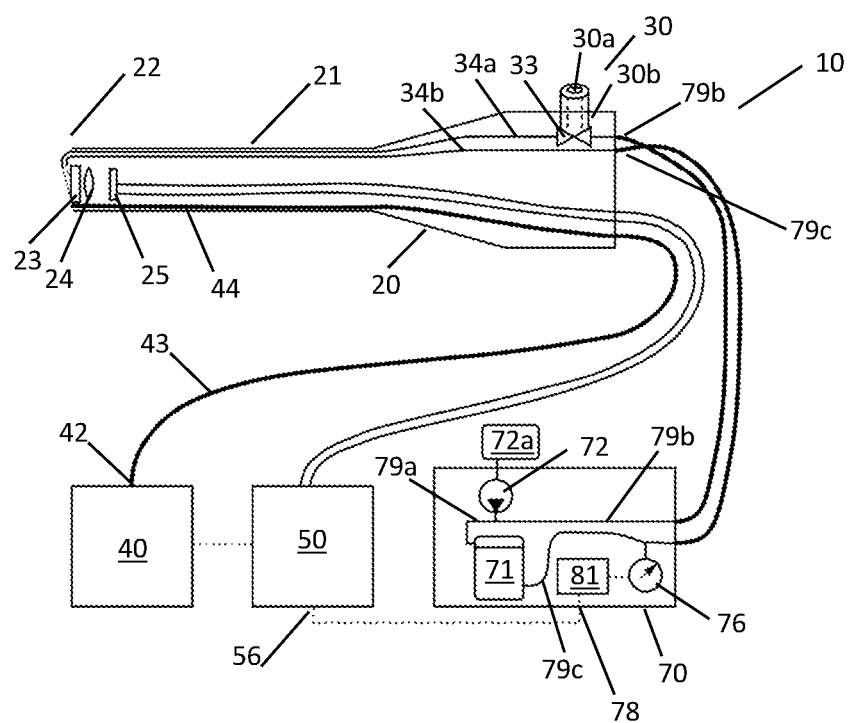
FIGS. 9A and 9B show schematic representations of two related endoscopic system wherein a flush mode is detected with reference to a pressure detector which may be part of the flush system or of an attached "plug"

FIG. 9A shows a schematic view of a primarily state-of-the-art endoscopic system 10 used in the field at the time of the filing of this disclosure. In addition, the system 10 includes a rinsing device 70 and a flush detection module 81. This flush detection module 81 can be a non-hardware addition to the existing system, for example, it can be an element of the CCU or any other appropriate on-board processor in the endoscopic system 10, such as an already present field-programmable gate array (FPGA), which are common elements of endoscopes. The system includes the endoscope 20 with a valve 33 and user interface for control of air and rinse liquid respectively. In the example system shown in FIGS. 9A and 9B, a mechanical valve 33 is used, and valve controls 30a and 30b include a dual function, single push button 30b with an opening 30a. The rinsing device 70 includes a pump 72 in communication with both the valve control 30 of the endoscope 20 as well as liquid reservoir 71. The pump 72 has or generates a positive pressure of an appropriate gas, such as air, nitrogen, or carbon dioxide, and may operate as a pump delivering positive pressure from the environment or as a valve, connected to a pressurized gas container 72a connected thereto. The pump 72 is connected by gas output line 79b to the valve 33 of the endoscope 20 as well as by gas pressurization line 79a to the rinsing liquid reservoir 71. The rinsing liquid reservoir 71 is further in communication through liquid output line 79c to the endoscope 20. In a first operating position, the valve vents gas from the pump 72 through the opening 30a into the environment, such as an operating room. In a second operating position, the opening 30a of the user interface 30 is obstructed, such as by the finger of the user, and the gaseous flow, instead of being vented to the environment, passes through rinsing gas duct 34a to the distal end 22 of the endoscope 20, permitting, thereby, the delivery of a gas to the surgical site, such as for the purpose of insufflation, delivery of a gas useful to the procedure, or providing a gaseous rinse of the distal end 22 of the endoscope 20. If, instead of simply covering the hole 30a, the single push button 30b is activated by, for example, being depressed, a third operating mode is engaged when the valve 33 seals the gas output line 79b, thereby redirecting the gaseous pressure to the liquid reservoir 71 through gas pressurization line 79a. The resultant increase in pressure on liquid reservoir 71 causes the rinse fluid to flow from the liquid reservoir 71 through liquid output line 79c and into the endoscope 20 to which it is connected. The rinsing fluid is then transferred by the rinsing liquid duct 34b to the distal end 22 of the shaft 21, where it may then be used to irrigate the operating theater and flush the distal end 22, and in particular can be used to rinse the distal light entrance surface 23 to remove any accumulated tissues, fluids, debris, etc. If the single push button 30b at user interface 30 toggled back to the previous position, and the hole 30a remains obstructed, gas from the pump 72 is again directed back through the gas duct 34a and can blow away any remaining rinsing fluid or debris, dry the distal light entrance surface 23, etc., in order to further improve the viewing conditions of the endoscope 20.

Pressure sensor 76, used to detect the instantaneous pressure in the system, can be connected to the liquid output line 79c connecting the reservoir 71 to the endoscope 20. The pressure sensor 76 generates signals that can be used by the present system to determine, without an electrical signal from the user interface 30, that a flush of the distal light entrance surface 23 is in progress, thereby triggering an alternative capturing mode and/or illumination mode, such as those previously discussed. The pressure sensor may be an element of the endoscope 20 or the rinsing device 70. Electronic signals generated by the pressure sensor 76 can be transmitted to a flush detection module 81 for processing. Flush detection signals can be transmitted from sensor signal output 78 to sensor signal input 56 at the CCU.

Figure 9B:
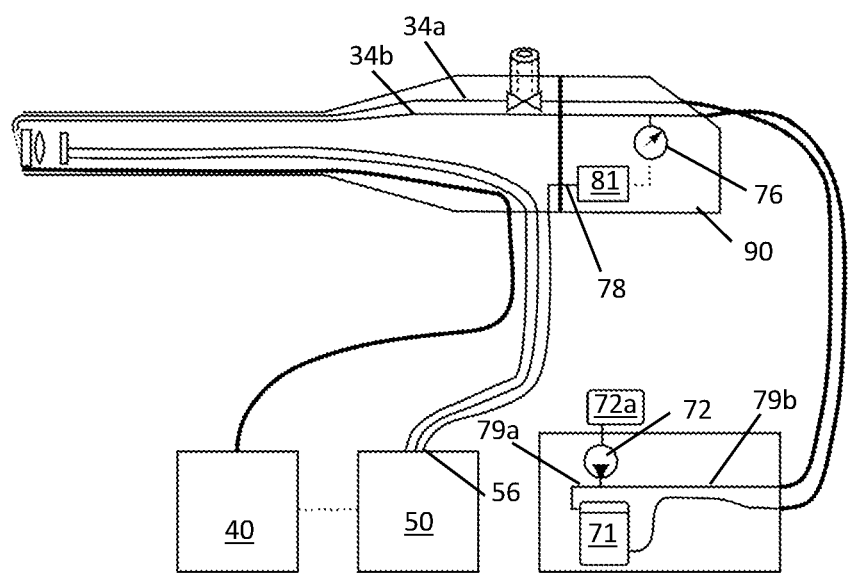

In some embodiments the pressure sensor 76 and/or flush detection module 81 can be elements of a "plug unit" 90 detachably connected to the endoscope 20, as shown in FIG. 9B. The plug unit embodiment shown in FIG. 9B has the added advantages including permitting the use of the present invention without the need to replace the entire endoscopic system 10, but rather simply replacing the plug unit (which can be a common element of an endoscopic system). It will be readily seen that most of the elements shown in FIG. 9A are also present in the embodiment of FIG. 9B, and therefore a discussion thereof will not be repeated. This plug element 90 can have all the necessary fluidic connections to deliver gas or liquid to the rinsing ducts 34a, 34b as well as electronic connections necessary with the endoscope to deliver any needed electrical power and/or carry the pressure signal to a camera control unit 50, for example by sensor signal output 78 to sensor signal input 56 at the CCU. Alternatively, electrical communication between the plug 90 and the CCU 50 can be by direct electrical connection. It should also be noted that the flush detection module 81 can be an element of the CCU rather than an element of the plug 90 or rinsing device 70.

While it is an objective of the present invention to permit the changing of illumination or capture modes to mitigate the negative user experience associated with a flush mode, simple readings of pressure signal alone are not always reliable indicators that a liquid flush is being performed. Variations in the measured pressure can occur when changes to the gas flow, discussed above, are made, as well as a result of other events that commonly occur in during endoscopic use, such as bumping or rapidly moving the instrument. It is therefore beneficial to provide further analysis of the pressure data in order to definitively determine the flush mode status.

Figure 10:
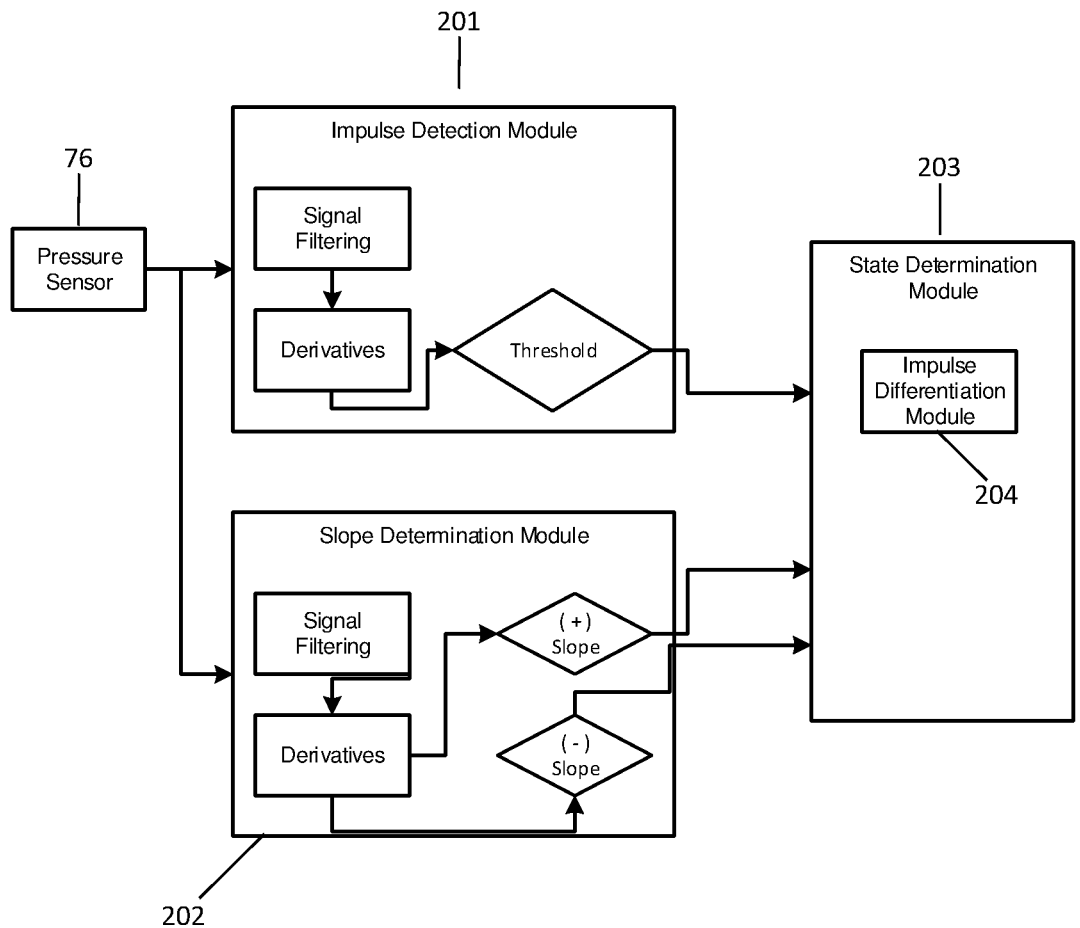
FIG. 10 is a schematic representation of various modules used to determine the flush state based on data received from a pressure sensor.

Referring now to FIG. 10, particularly as it relates particularly to FIGS. 9A and 9B, the flush detection module 81 may include one or more additional submodules that receive a pressure signal from the pressure sensor 76 and therewith make one or more determinations as to the state of a light entrance surface flush. In the present example, an impulse detection module 201, a slope determination module 202, and a state determination module 203 may be included in the flush detection module 81. Pressure data is collected by the pressure sensor 76 and delivered to the impulse detection module 201 and the slope determination module 202. The data stream received by each module may be filtered as appropriate. Use of the impulse detection module 201 in conjunction with the slope determination module 202 in the analysis of the pressure sensor 76 data, enables the identification of a liquid rinse state.

The impulse detection module 201 detects rapid fluctuations in the pressure of the rinsing system. As discussed above, these fluctuations may be a result of a variety of occurrences possible during the operation of the endoscopic system, including the depression of single push button 30b and the resulting toggling of valve 33; thus impulse detection module 201 may perform signal processing such as performing calculations based on pressures at a plurality of times to determine if the first pressure disturbance is likely due to an opening of the valve 33 or another cause such as, for example, rapid movement of the endoscope 20 or another element of the system 10 such as the fluid reservoir 71. In order make this determination, the impulse detection module 201 may compare pressure values at two or more distinct times to determine if a pressure fluctuation, such as a series of pressure spikes and/or oscillations, has occurred that exceeds a pre-defined impulse threshold. If the pressure fluctuation is greater than the impulse threshold, the impulse differentiation module 204 initiates a timer. If the pressure fluctuations continue to be greater than the impulse threshold when the timer reaches the end of a predetermined impulse duration time, the impulse differentiation module 204 may determine the first pressure disturbance is not due to opening the valve, but rather due to some other sustained cause not related to the flush mode. Conversely, if the pressure fluctuation stops or decreases to less than the impulse threshold before the timer reaches the predetermined impulse duration time, the impulse differentiation module 204 may determine the pressure disturbance is likely due to closing the valve 33 and a flush impulse detected flag is set, noting that the impulse criteria have been met, and the state determination module 203 notes this flush impulse detected flag.

The slope determination module 202 detects a longer duration fluctuation in the pressure value by receiving the pressure signal from the pressure sensor 76 and performing signal filtering and other signal processing calculations, including performing derivatives, to determine the magnitude and direction (positive or negative) of the slope, resulting in a determination of a positive (pressure increasing), negative (pressure decreasing) or zero slope (no appreciable change in pressure) of the overall pressure in the flush system.

The state determination module 203, having noted the flush impulse event flag from the impulse differentiation module 204 and the value of the slope of the pressure from the slope determination module 202 determines the state of a flush event. A flush impulse detected flag coupled with a positive slope is generally indicative of the activation of the single push button 30b resulting in the beginning of a liquid flush event. A flush impulse detected flag coupled with a negative slope is generally indicative of the activation of the single push button resulting in the end of a liquid flush event. A positive or negative pressure slope without a flush-impulse event and/or an impulse event occurring with no slope are not interpreted by the state determination module 203 as being indicative of a change in the liquid rinse state. Thus, analysis of the output data from the impulse detection module 201 and the slope determination module 202, the state determination module 203 may determine whether a light entrance surface flush event is active and communicate determination to the CCU 50 and/or light source 40 to make one or more adjustments to the image processing or light source control previously discussed.

Figure 11A:
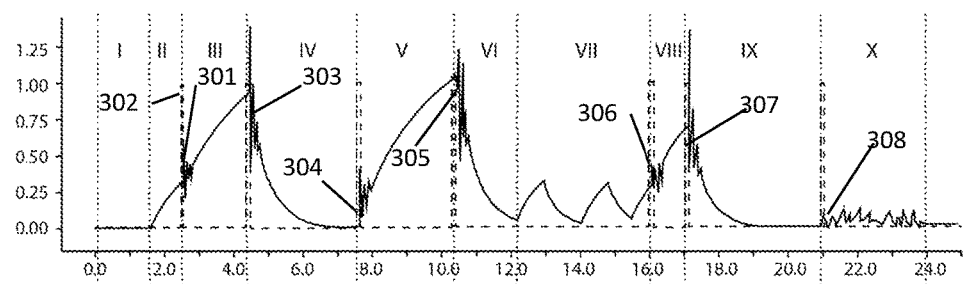
FIG. 11A shows raw pressure sensor data and impulse detection regions.

In order to illustrate typical operating conditions of the system described in FIGS. 9-10, attention is now drawn to FIG. 11A-D illustrating pressure data collected by the pressure sensor 76 over a 25 second run time for a variety of use cases for the system 10. The graphs show time in seconds on the X-axis, which, for illustrative purposes, includes a range from 0 seconds to 25 seconds. A number of discrete time ranges, indicated by Roman numerals, I-X, illustrate the detection of use events by the flush detection module 81. The graphs show pressure values P detected by the pressure sensor, and displayed as a percentage P (%) (solid line) of a maximum pressure $P_{MAX}$. $P_{MAX}$ may be the maximum pressure provided by the rinsing device 70, or another arbitrary, normalized value. FIGS. 11A.11B and 11D show raw data collected by the pressure sensor 76, while the data presented in FIG. 11C has been filtered to remove data spikes and noise and to smooth the overall curve.

Figure 11B:
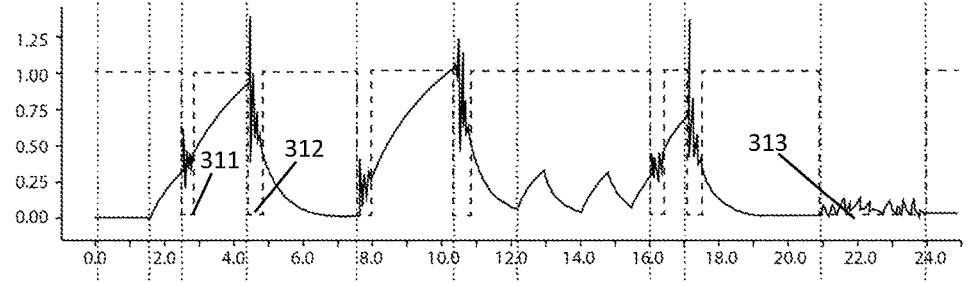
FIG. 11B shows raw pressure data and indications of impulse event timers.
Figure 11C:
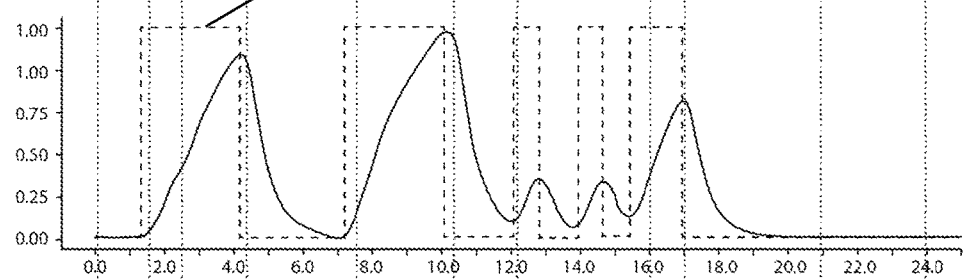
FIG. 11C shows smoothed pressure data and indications of a positive slope.
Figure 11D:
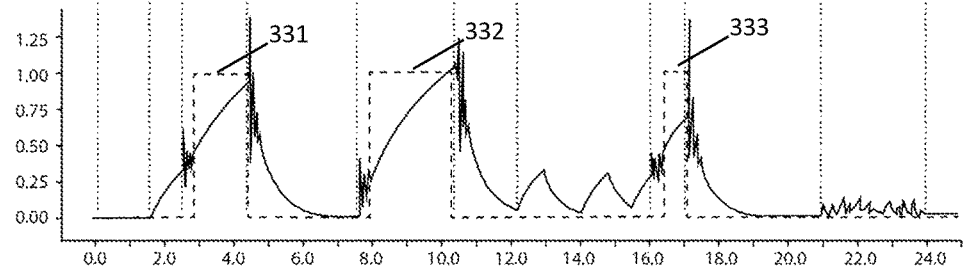
FIG. 11D shows raw pressure data and indications of a flush mode.

Each of FIGS. 11A-D also show an indicator trace (dashed line), the relevance of which is discussed below. FIG. 11A shows an impulse detector output indicating a reading of 1.00 when an event is detected and a 0.00 when no event is detected. FIG. 11B shows an impulse event timer trace, which is shown as a value of 1.00 when the timer is not counting, and a value of 0.00 when the timer is counting. FIG. 11C shows a slope indicator trace, reading 1.00 when there is an overall positive slope, and 0.0 when there is an overall negative slope or zero slope. FIG. 11D shows a flush indication trace which is shown as a value of 1.00 when a flush event has been detected and a 0.00 when there is no flush occurring.

In a first example use case, depicted during the time ranging from 0.0 s to about 7.5 s (time ranges I-IV), the pump may be active throughout or the user may activate the pump, close the air valve 30a, depress the single push button 30b to open the valve 33 to initiate a light entrance surface flush, again press the single push button 30b to close the valve 33 to stop the flush and open the air valve 30a. Beginning with range I, at time T=0.0 s, the pump may be activated to begin pumping gas such as air, nitrogen, or $CO_2$ into the gas pressurization line 79a and fluid output line 79b connected thereto. The gas from pump 72 may freely flow out of the air valve 30a from time T=0.0 s to T=1.5 s and vent to the atmosphere, resulting in flat pressure signal indicating no pressure building up in the flush system. In range II, starting at time T=1.5 s, the user closes the air valve 30a by, for example, covering the opening with a finger, which blocks the flow of the gas exiting the endoscope 20 to the atmosphere, resulting in a flow of the gas through the rinsing gas duct 34a of the endoscope 20 and pressure begins to build in the system. However, it can be seen by the data that this closing of the air valve 30a does not result in an impulse event. The pressure may increase in a generally smooth manner in region II from time T=1.5 s until just before time T=2.5 s. During this period, the slope determination module 202 receives the pressure signal from the pressure sensor 76 and determines the magnitude and direction of the slope. In range II, the slope of the filtered signal is positive, indicating that pressure is building in the system, as can be seen by the dashed line at position 321 in FIG. 11C.

At approximately time T=2.5 s, the user closes the valve 33 by depressing the single push button 30b, sealing thereby gaseous flow from the pump to the rinsing gas fluid duct, and redirecting pressure to the rinsing liquid reservoir 71, resulting in rinsing liquid being delivered through the rinsing liquid duct 34b to the distal end 22 of the endoscope 20. This change in the system state causes a first pressure disturbance 301 seen as pressure spikes and oscillations seen in FIG. 11A. This first pressure disturbance 301 is be detected by the impulse detection module 201, which flags the impulse event at position 302 as meeting the predetermined threshold requirements. The impulse differentiation module 204 may then start an impulse event timer, indicated in FIG. 11B at 311. If the timer reading of the impulse differentiation module 204 indicates a flush impulse has been detected, the state determination module 203 may query the slope determination module 202. If, as in this case, there is an impulse event flag 302, the timer meets the requirements to indicate a flush impulse event are met, and the slope is positive (as it is in range II-III) 321, then the state determination module 203 determines that light entrance surface flush event is active and communicates this determination to the CCU 50 and/or the light source 40 which engages the second illumination and/or capture mode.

The pressure continues to rise smoothly throughout range III, from approximately time T=2.5 s-4.5 s. At approximately time T=4.5 s, a second pressure disturbance 303 occurs when the user engages single push button 30b to open the valve 33. As before, the impulse detection module analyzes the pressure disturbance 303 and flags it as an impulse event. Again, the impulse differentiation module begins a timer indicated at 312 and determines that a flush impulse has been detected. State determination module 203 then queries slope determination module 202 which indicates that the pressure slope is now negative. This indicates to the state determination module that the light entrance surface flush event has ended and sends this determination to the CCU 50 and/or light source 40 which returns the system to the first illumination and/or capture mode. The entire period of the flush event has been therefore identified and is shown as at 331 in FIG. 11D.

Throughout range IV, the pressure in the flush system decreases back to a baseline, prior to a further pressure disturbance 305 at approximately T=7.5 s. Again, the state determination module, through the process discussed in the previous paragraph, determines that a flush event is occurring, and the second illumination and/or capture mode is engaged throughout range V, ending at approximately T=10.5 s, where another flagged pressure disturbance 305 is detected, which, coupled with the decreasing slope in range VI, indicates the end of a flush event, triggering, thereby, a return to the first illumination and/or capture mode. This flushing period is indicated on FIG. 11D at 332.

The importance of the method described herein can be further demonstrated with reference to range VII, from approximately T=12 s-15 s. At approximately T=12 s, the air valve 30a is closed, delivering a gaseous flow to the endoscope distal end 22, as in range II. At approximately T=13 s, the air valve 30b is opened again, ceasing air flow, closed again at time T=14 s, resuming air flow, and opened again at approximately T=14.9 s. Rapidly delivered spurts of air to the distal end of the endoscope such as shown in region VII are commonly executed by users to dry the distal light entrance surface 23 or blow off any residual droplets or debris. However, as there is no impulse event detected by impulse detection module 201, the first illumination and/or capture mode is maintained throughout region VII. Alternately, in some embodiments, the monitoring of the slope by the slope determination module 202 after a liquid flush event has ended, can help to identify further flush events, such the gas flush of the distal light surface seen in region VII, and it may be desired to remain in the second video settings mode during this period, as fast-moving droplets on the distal light entrance surface may be cause unwanted visual artifacts. Therefore, it may be desirable to wait for the indication of a flat slope (for example, at T=19 s-21 s in Region IX) or for a predetermined time after the end of a flush event is detected.

A final flush of the distal light entrance surface 23 is begun at time T=15.5 s, and continues to about time T=17 s, within region VIII, as can now be readily understood by the impulse events 306 and 307 shown in FIGS. 11A, the timer events shown in FIG. 11B, and the corresponding slope determination states shown at those times in FIG. 11C, resulting I the determination of flush event 333 shown in FIG. 11D.

Lastly attention is drawn to region X of FIG. 11. At approximately T=21 s, an impulse event 308 occurs and is detected by the impulse detection module 201 as meeting the required threshold value and flagging it as an impulse event. The impulse differentiation module 204 then begins a timer as indicated by the 0.00 trace 313 in FIG. 11B. The impulse event exceeds the timer threshold, and therefore the state determination module 203 determines that the impulse event does not indicate a flush impulse event, and therefore the first illumination and/or capture mode is maintained throughout region X.

Figure 12:
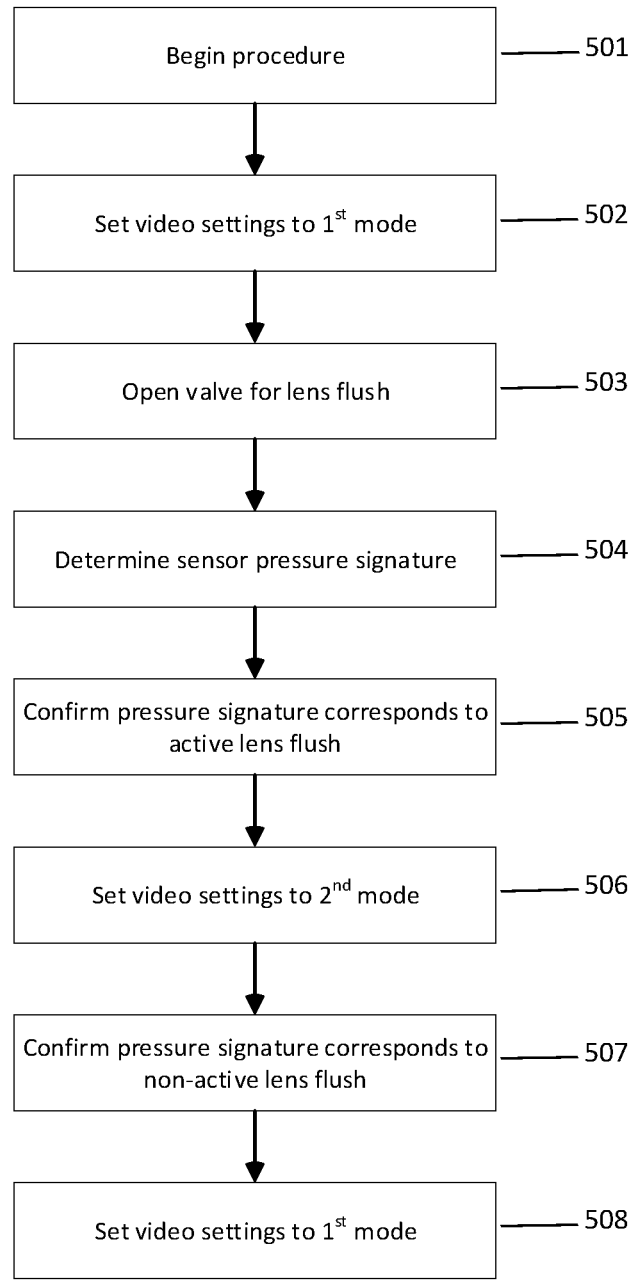
FIG. 12 is a flowchart showing the various steps in determining a flush event and related video mode settings.

FIG. 12 describes the method of operation of the system 10. At step 501 a procedure is started, and the video settings are set 502 to a first illumination and/or capture mode. During the procedure, the valve 33 is opened 503 to perform a distal light entrance surface rise. The impulse detection module 201 determines that the pressure signal matches a particular threshold, and the impulse differentiation module 204 determines that the duration of the impulse meets the conditions indicating a flush impulse, thereby matching a "pressure signature" 504 and a flush impulse event is flagged. The pressure signature may then be confirmed 505 by analysis of the slope by the slope determination module. If the active flush event is indicated by the state determination module 203, the second illumination and/or capture modes are engaged 506. Once the state determination module 203 confirms, with reference to the impulse detection module 201, the slope determination module 202 and the impulse differentiation module 204, that the flush event is complete 507, the illumination and/or capture settings are reset 508 to the first mode.

Example embodiments of the methods and systems of the present invention have been described herein. As noted elsewhere, these example embodiments have been described for illustrative purposes only and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents.

While the invention has been described in connection with various embodiments, it will be understood that the invention is capable of further modifications. This application is intended to cover any variations, uses, or adaptations of the invention following, in general, the principles of the invention, and including such departures from the present disclosure as, within the known and customary practice within the art to which the invention pertains.

The invention claimed is:

1. An endoscopic system comprising:
an endoscope comprising a shaft, a light entrance surface at a distal end of the shaft, an electronic image sensor to collect light passing through the light entrance surface; a liquid rinsing duct in the shaft for conducting a rinsing fluid from the proximal end of the endoscope to the light entrance surface for rinsing the light entrance surface, a gas rinsing duct in the shaft for conducting a gas from the proximal end of the endoscope to the light entrance surface, and a valve for opening and closing the gas rinsing duct;
a rinsing device comprising a pump with fluid connections to a rinsing liquid reservoir and the endoscope;
a pressure sensor for detection of a pressure with a fluid connection of the rinsing device;
a flush detection module coupled to the pressure sensor; and
a user interface operable to control the valve.

2. The endoscopic system of claim 1, wherein the user interface means to control the valve comprises three operation modes: a first operation mode, wherein gas may pass out of the user interface into the environment, a second operation mode, wherein gas is directed through the gas rinsing duct, and a third operation mode, wherein the valve is closed, causing gas flow from the pump to be blocked.

3. The endoscopic system of claim 2, wherein the flush detection module comprises an impulse detection module, a slope determination module and a state determination module.

4. The endoscopic system of claim 3, further comprising a camera control unit in communication with the flush detection module and the image sensor and operable, when a flush event is detected by the state determination module, to switch from a first video settings mode to a second video settings mode.

5. The endoscopic system of claim 4, further comprising a light source, the light source in communication with the camera control unit, and wherein the switching from the first video settings mode to the second video settings mode comprises the step of decreasing an illumination intensity.

6. The endoscopic system of claim 4, wherein the flush detection module is an element of the camera control unit.

7. The endoscopic system of claim 1 further comprising a plug element, and wherein the plug element is detachably connected to the endoscope.

8. The endoscopic system of claim 7, wherein the flush detection module and the pressure sensor are elements of the plug element.

* * * * *